United States Patent [19]

Burgess et al.

[11] Patent Number: 4,944,753
[45] Date of Patent: Jul. 31, 1990

[54] METHOD FOR PRODUCING RETRO-STERNAL SPACE

[76] Inventors: Frank M. Burgess; Neal B. Burgess, both of 610 Amber Dr., Huntington Beach, Calif. 92648

[21] Appl. No.: 249,123

[22] Filed: Sep. 26, 1988

[51] Int. Cl.$^5$ ............................................. A61B 17/00
[52] U.S. Cl. ........................................ 623/16; 606/86; 606/151
[58] Field of Search ................. 623/16, 66; 128/92 R, 128/92 VK, 92 YF, 334 R, 335, 334 C

[56] References Cited

U.S. PATENT DOCUMENTS 4,802,477 2/1989 Gabbay ........................ 128/334 R X Primary Examiner—Richard J. Apley
Assistant Examiner—David F. Crosby
Attorney, Agent, or Firm—David Weiss

[57] ABSTRACT

A method and device for producing an artificial retro-sternal tunnel or space at the conclusion of a sternotomy, for precluding cutting the heart when the sternum is severed during a subsequent or re-do sternotomy involving the same patient. During closure of the longitudinally severed sternum, an implantable elongate member having a length approximately the length of the sternum is disposed longitudinally along the severed sternum and opposing the sternum's posterior surface, and the disposed member is secured to the sternum during closure. In the event a subsequent sternotomy is required for the same patient, the surgeon positions a sternum cutting device at one end of the sternum overlying the implanted member, and longitudinally severs the sternum with the implanted member, which may include a hard elongated inner member, providing a pathway and/or shielding the patient's heart from being unintentionally cut by the cutting device. Alternatively, the implanted member may be lengthwise withdrawn prior to the surgeon's severing the sternum during the re-do sternotomy, to provide a retro-sternal tunnel in ths space formerly occupied by the removed member, and the surgeon thereupon longitudinally serves the sternum along the retro-sternal tunnel so provided.

15 Claims, 2 Drawing Sheets

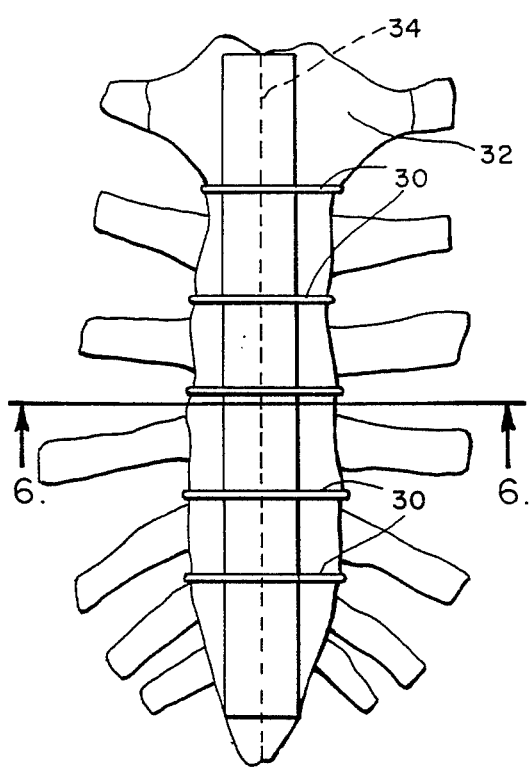
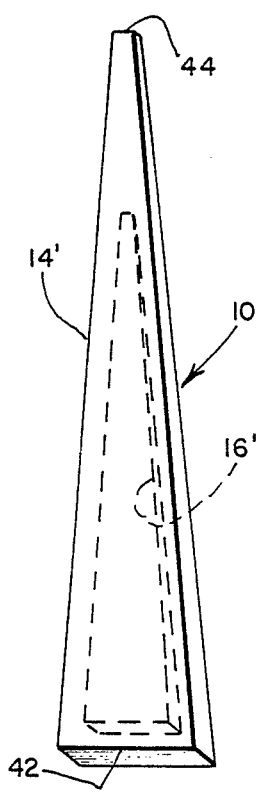
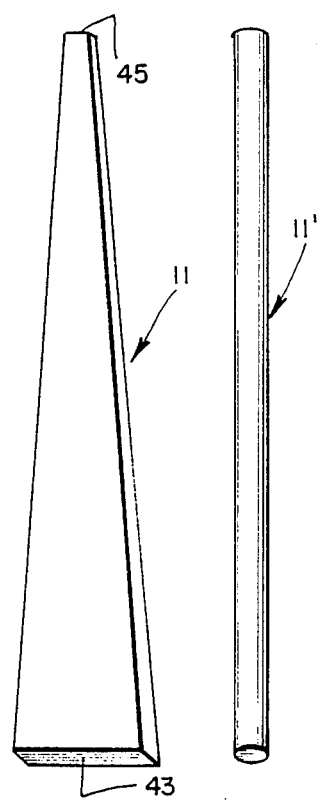
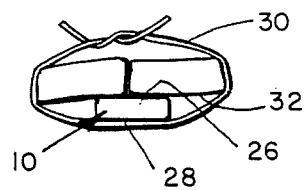
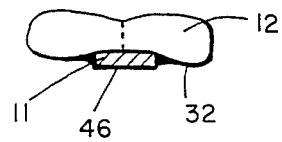
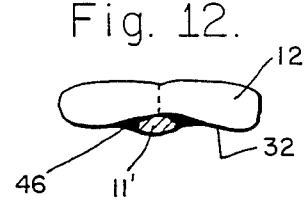
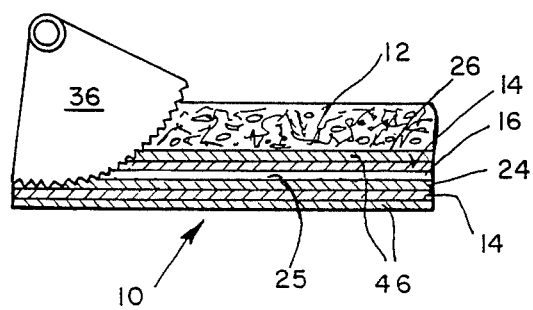
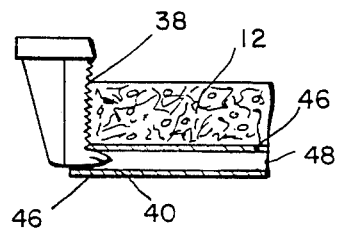

METHOD FOR PRODUCING RETRO-STERNAL SPACE

BACKGROUND OF THE INVENTION

This invention relates to surgical devices and methods, and more particularly to devices and methods for assuring availability of a retro-sternal space following a sternotomy.

During the years since the first successful "open heart" operation using extracorporeal circulation was performed, the number and complexity of surgical procedures involving the heart which have been developed and are being electively performed have increased remarkably. Congenital and acquired lesion of the heart in patients of all ages are routinely treated surgically in most developed nations throughout the world. In the United States alone, an estimated 200,000 operations on the structures of the heart are performed annually.

The beneficial consequences from heart surgery combined with acceptable morbidity and morality statistics have produced a level of confidence among physicians which allows them to prescribe surgical intervention on multiple occasions for the same patient. Reoperation on the heart is not uncommon; at least five separate heart operations on the same patient are known to have been performed.

The sternum and the underlying heart are normally anatomically separated by a distance which, although varying with the individual, is typically one to two centimeters. In effect, there exists a tunnel between the internal or posterior surface of the sternum and the front or anterior surface of the heart and pericardium, often referred to as "the retro-sternal space." In nearly all cardiac surgical procedures, access to the heart and great vessels is obtained through a median sternotomy whereby the sternum is longitudinally severed with a specially designed saw and the severed sternal edges are spread apart. During an initial sternotomy the existence of the retro-sternal space or tunnel longitudinally underlying the sternum decreases the probability of inadvertent laceration of the heart or great vessels as the saw cuts through the sternum.

While initial sternotomy is considered to carry an extremely low risk as respecting this type of injury, the risk is substantially increased for a subsequent or "re-do" sternotomy. Obliteration of the retro-sternal space following a sternotomy may permit the anterior wall of the heart to bond to the posterior surface of the sternum. Adhesions which form between the sternum and the heart are evenly distributed over the structures of the heart; however, in most cases the wall of the right ventricle and right atrium are adherent to the sternum. If during a re-do sternotomy the sternal saw enters either of these chambers, the occurrence is immediately apparent but nonremediable until the cut edges of the sternum are spread apart to expose the heart. As the sternal edges are spread the rent in the violated heart chamber is enlarged due to the adhesions between the heart and the sternum in the vicinity of the edges of the laceration. It is considered that the entering of a heart chamber during re-do sternotomy creates a life threatening situation.

SUMMARY OF THE INvENTION

The method and device of the present invention eliminates or greatly decreases the risk of inadvertent laceration of the heart and/or great vessels during re-do sternotomy. An artificial retro-sternal space or tunnel is created by implanting the device of the invention, during wound closure, immediately beneath the sternum of a patient undergoing cardiac surgery. Should reoperation become necessary, the patient's subsequent sternotomy will be facilitated by means of the previously implanted device of the present invention.

The method of the present invention, performed during a sternotomy, comprises the steps of providing an elongate implantable device having a length approximately the length of the patient's sternum, disposing the elongate device longitudinally along and posteriad the patient's sternum, and securing the disposed device to the sternum. The above steps are conveniently carried out during sternal closure, with the elongate device being secured to the sternum and facing the sternum's posterior surface, by means of the sternal wires which are ordinarily used to bring and secure the cut edges of the sternum together In such manner, the implanted elongate device underlies the sternum's severed edges when closed.

The preferred embodiment of the elongate device comprises an elongate member or envelope consisting of a flexible and resilient material such as silicone rubber, the envelope containing an elongate strip which is flexible although more rigid than the envelope and constructed of a relatively hard material such as a polycarbonate, nylon, polypropylene or other suitable plastic. The width and thickness of the device will vary with the individual, but may typically fall within the ranges 2 to 5 centimeters and 0.5 to 1.0 centimeter, respectively, for most human adults.

During a re-do sternotomy, or a sternotomy subsequent to the sternotomy during which the preferred embodiment of the device of the present invention had been implanted, the method of the present invention is continued to be utilized by the surgeon and includes the further steps of positioning a sternum cutting device or saw at an end of the elongate member and longitudinally severing the sternum while using the elongate device as a pathway and/or shield for precluding unintentional cutting of the patient's heart and/or great vessels. The somewhat hard plastic strip acts as a barrier between the surgeon's saw blade and the patient's heart and vessels. The elongate device is removed by the surgeon after the sternum has been severed.

A second embodiment of the device of the present invention provides an elongate member of an implantable material and adapted for being withdrawn prior to severing the sternum during the subsequently performed sternotomy. In such case, the method of the present invention includes the steps of lengthwise withdrawing the elongate member during the subsequently performed sternotomy, to provide a retrosternal tunnel in the space formally occupied by the removed member, and longitudinally severing the sternum along the retro-sternal tunnel. The tunnel, which is produced during the time period between the sternotomy during which the elongate member was implanted and the subsequent sternotomy, utilizes the ability of the human body to form a thin fibrous layer or capsule about foreign material placed in human tissue. Accordingly, when the elongate member of the second embodiment is withdrawn during the subsequent sternotomy, the retro-sternal tunnel comprises an elongate fibrous tissue envelope disposed longitudinally along and posteriad the sternum, separating the sternum from the heart, and may be used by the surgeon as a pathway for the sternal saw while severing the sternum for precluding unintentional laceration of the patient's heart and/or great vessels.

BRIEF DESCRIPTION OF THE DRAWINGS

The novel features which are believed to be characteristic of the invention, together with further advantages thereof, will be better understood from the following description considered in connection with the accompanying drawings in which preferred embodiments of the device of the invention and of the method for practicing the invention are illustrated by way of example, and wherein like reference numerals are utilized to indicate like components. It is to be expressly understood, however, that the drawings are for the purpose of illustration and description only, and are not intended as a definition of the limits of the invention.

FIG. 5 is a view of the posterior surface of a severed sternum, showing the device of the present invention in place and secured to the sternum after sternal closure;

FIG. 6 is a cross-sectional view of the sternum and device shown in FIG. 5, taken along the line 6—6 in the direction of the appended arrows;

FIG. 7 is a fragmentary longitudinal cross-sectional view of a sternum with the implanted device of FIGS. 1 and 2, shown with one type of sternal saw severing the sternum during a re-do sternotomy;

FIG. 8 is a perspective view of a second configuration of the preferred embodiment of the device according to the present invention, indicating an elongate chamber therein in phantom;

FIG. 9 is a perspective view of an alternative embodiment of the device according to the present invention;

FIG. 10 is a cross-sectional view of a sternum and the implanted device shown in FIG. 9;

FIG. 11 is a perspective view of a second configuration of the alternative embodiment of the device according to the present invention;

FIG. 12 is a cross-sectional view of a sternum and the implanted device of FIG. 11; and FIG. 13 is a fragmentary longitudinal cross-sectional view of a sternum and a retro-sternal tunnel formed after removal of the implanted device of FIG. 9 or FIG. 11, shown with a second type of sternal saw severing the sternum during a re-do sternotomy.

DESCRIPTION OF THE PREFERRED EMBODIMENTS

Figure 1:
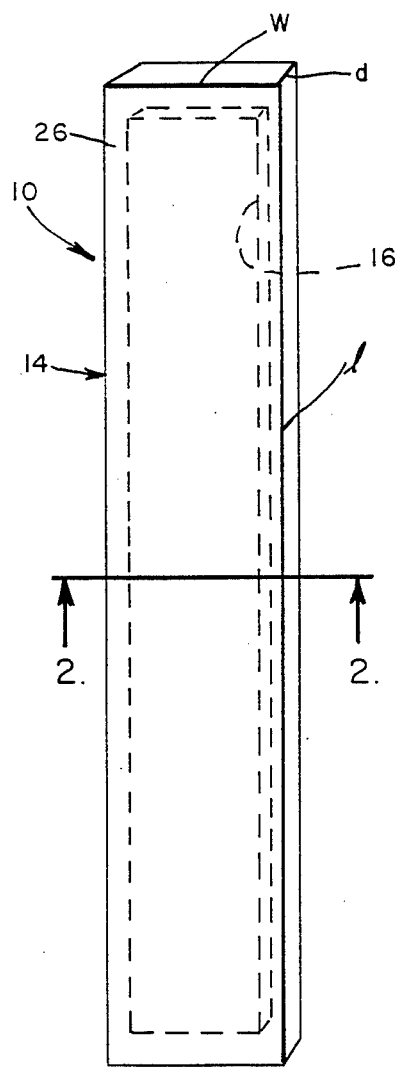
FIG. 1 is a perspective view of a preferred embodiment of the device of the present invention, indicating an elongate chamber therein in phantom.
Figure 3:
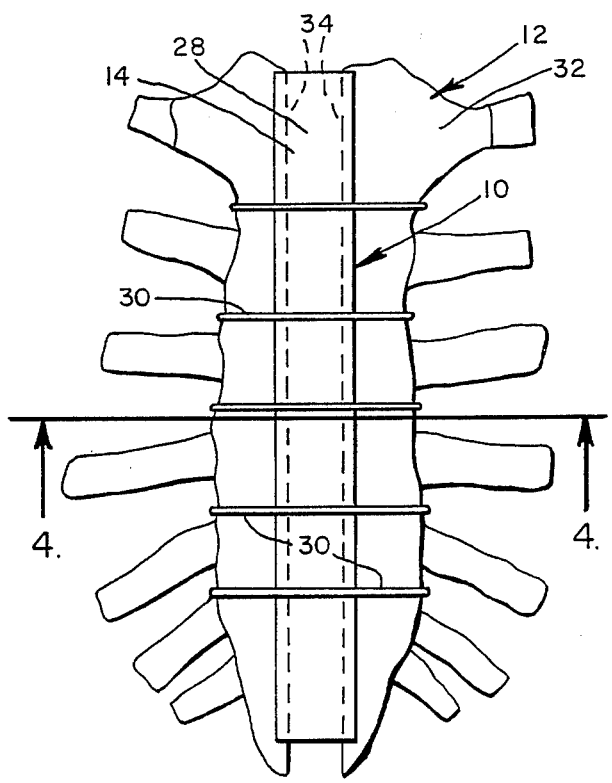
FIG. 3 is a view of the posterior side of a severed sternum showing the device of the present invention in place for being secured to the sternum during sternal closure.

Referring to FIG. 1, the preferred embodiment of the retro-sternal tunnel device 10 of the present invention includes an elongate member 14 which has a length 1 approximately the length of a sternum 12 (as better shown in FIG. 3). The width w of the member 14 may be approximately the same as or narrower than the width of the sternum 12; and the depth d of the member 14 may be approximately the depth of the retro-sternal space, or somewhat smaller. Although these dimensions may vary with an individual patient, typical ranges of these dimensions for human adults may include lengths 1 between approximately 15 and 28 centimeters, widths w between approximately 2 and 5 centimeters and depths d between approximately 0.3 and 1.5 centimeters. The foregoing dimensions are given as examples only, and are not to be deemed exclusive of other dimensions outside the stated ranges.

The elongate member 14 contains an interior chamber 16 having dimensions slightly smaller than the outside dimensions 1, w, d of the member 14. The member 14 is made of an implantable material which is flexible and resilient, such as conventional implantable medical grade silicone rubber. The member 14 may be formed by various processes; in an example of one such process, a generally rectangular bottom portion 18 (FIG. 2) of length 1 and width w may be molded with a longitudinal channel 20 slightly shorter than the length of the member 14; a lid 22 of length 1 and width w may be molded and sealed to the bottom member 18 to form the chamber 16. Inserted within the chamber 16 is a strip 24 which, although somewhat flexible, is harder and more rigid than the outer member 14, and may be made of such material as polycarbonate, nylon or polypropylene. The plastic strip 24 is preferably slightly smaller in each dimension than the dimensions of the chamber 16, preferably but not necessarily lying freely within the chamber 16. Alternatively, the outer member 14 may be formed about the inner strip 24 such as by conventional molding techniques. It is apparent that the outer member 14 forms a sealed envelope for containing the inner strip 24, and includes a first outer surface 26 and a second outer surface 28 with the inner strip 24 longitudinally disposed therebetween and, in this example, with the surface 25 of the strip 24 along its length/width dimensions being generally parallel to the outer member surfaces 26 and 28.

During wound closure at the conclusion of cardiac surgery, the surgeon closes the severed sternum usually by placing a plurality of sternal wires (conventionally stainless steel) in longitudinally spaced relation transversely around or through both halves of the sternum, permitting the severed edges of the sternum to remain separated until all wires are in place. Conventionally, the surgeon then pulls the wires taut to bring the severed edges of the sternum together in mid-line, and the wire ends are then tied or twisted to maintain the sternum closed.

Figure 4:
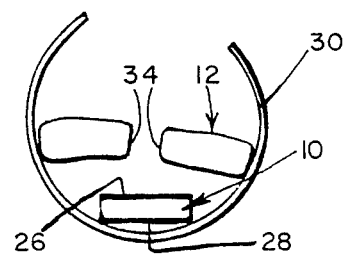
FIG. 4 is a cross-sectional view of the sternum and device shown in FIG. 3 taken along the line 4—4 in the direction of the appended arrows.

In practicing the method of the present invention, the elongate device 10 is implanted opposing (and preferably against) the posterior surface of the sternum, longitudinally disposed along the mid-line of the sternum. During the sternal closure procedure (see FIGS. 3 and 4), the wires 30 passing through or around the sternum 12 form a sling into which the device 10 is placed, with the surface 26 of the outer member 14 being disposed longitudinally along the sternum 12 and opposing the sternum's posterior surface 32 before the sternum's severed edges are closed. When the ends of the wires 30 are pulled to bring the severed edges of the sternum 12 together and tied or twisted, to close the sternum 12 as shown in FIGS. 5 and 6, the wires' 30 contact with the second surface 28 of the member 14 urges the device 10 toward the sternum 12 and causes the first surface 26 of the resilient or pliable outer member 14 to contact the sternum's posterior surface 32 and to conform thereto where contacted. In such manner the flexible envelope 14 and the contained plastic strip 24 underlie the sternum 12—preferably including the sternum's severed edges 32—when the sternum 12 is closed at the conclusion of the sternotomy, and are thereby implanted in the retrosternal space between the sternum and the heart. Since it is usual for the body to produce a layer of fibrous tissue about implanted foreign material, after implantation of the device 10 a fibrous tissue capsule or envelope of approximately 150 to 300 micra wall thickness will form about the elongate device 10.

In the event that a subsequent cardiac operation is to be performed on the same patient, the implanted device of the present invention is utilized to facilitate the severing of the patient's sternum during the re-do sternotomy. The surgeon removes, in conventional manner, the sternal wires which were placed at the conclusion of the previous operation. He may then initiate cutting of the sternum with a sternum cutting device such as an arcuate oscillating type saw blade 36, as shown in FIG. 7, starting at one end of the sternum 12 typically at the xiphoid process or the sternum's caudal end. Upon initially cutting through the depth of the sternum 12, further depth penetration of the saw blade is limited by the saw blade's contacting the hard inner strip 24 and the surgeon's responding to such contact as he guides the saw blade along the sternum 10, for avoiding inadvertent laceration of the heart and/or great vessels.

Alternatively, during the re-do sternotomy the surgeon may identify and expose the end of the elongate device 10 near the xiphoid process or the sternum's caudal end, by opening the fibrous tissue capsule 46 (see FIG. 7) at such end. The surgeon then removes, in conventional manner, the sternal wires which were placed at the conclusion of the previous operation. Next, the surgeon opens the located end of the elongate outer member 14 to expose the inner chamber 16 and the inner strip 24, and inserts a sternal cutting device such as a reciprocating type saw blade 38 having a foot 40 (of the kind shown in FIG. 13). The surgeon inserts the foot 40 into the chamber 16 and resting upon the top surface 25 of the elongate inner strip 24 (FIG. 7), for limiting the depth of penetration of the saw blade 38.

Accordingly, using the elongate hard strip 24 as a shield, the surgeon proceeds to longitudinally sever the sternum 12 along the retro-sternal tunnel provided by the device 10, after which the surgeon removes the device 10 from the wound allowing the surgeon to proceed with the operation. Another elongate device 10 will be implanted (as previously described) during wound disclosure.

Turning to FIG. 8, there is shown a second configuration of an elongate device 10' of the preferred embodiment of the device 10 shown in FIG. 1. The device 10' is of tapered configuration along the longitudinal dimension as shown in FIG. 8, in width and/or in depth. In one such example of such configuration, the width at one end 42 of the elongate device 10' may be in the range of approximately 2 to 5 centimeters, with a width of perhaps 0.5 centimeters at the other end 44 of the tapered elongate device 10'. In such example, the depth of the elongate device 10' may be either uniform (typically between approximately 0.3 and 1.5 centimeters throughout its length), or its depth may progressively decrease along its length. In an example of decreasing depth, the depth at the one end 42 may be between approximately 0.3 and 1.5 centimeters and decreasing to perhaps approximately 0.25 centimeter at the other end 44. These dimensions, which may vary with an individual patient, are given as examples only and are not to be deemed exclusive of other dimensions outside the stated dimensions or ranges thereof.

Figure 2:
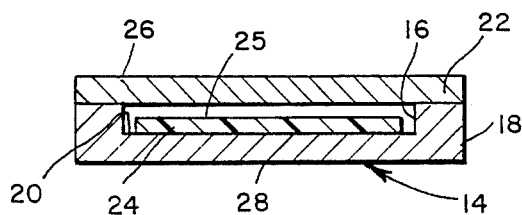
FIG. 2 is a cross-sectional view of the device of FIG. 1, taken along the line 2—2 in the direction of the appended arrows.

Except for its taper, the alternative configuration of the retro-sternal tunnel device 10' is similar to the device 10 described in FIGS. 1 and 2. The elongate member 14' contains an interior chamber 16' having dimensions slightly smaller than the outside dimensions of the member 14'. The member 14' is made of implantable material which is flexible and resilient, such as conventional implantable medical grade silicone rubber. Inserted within the chamber 16' is a strip (not shown) which, although somewhat flexible, is harder and more rigid than the outer member 14', and may be made of such material as polycarbonate, nylon or polypropylene. This strip is similar to the strip 24 shown in FIG. 2, except that the plastic strip of the alternative device 10' may be tapered, is preferably slightly smaller in each dimension than the dimensions of the tapered chamber 16', preferably but not necessarily lying freely within the chamber 16'.

The method of the present invention utilizing the tapered retro-sternal tunnel device 10' is practiced in tho same manner as when utilizing the device 10 of FIG. 1. However, during the sternal closure procedure, the tapered device 10' will be longitudinally disposed along the sternum 12 with the wider end 42 of the tapered device 10' situated at the caudal end of the sternum 12. The decreased width at the other end 44 of the tapered device 10' decreases any likelihood of interference with the mammary artery. It can be appreciated that the hard strip, with its decreasing width to conform to the chamber 16' and accordingly its shorter length, will likely not extend along the complete length of the sternum 12 when underlying the sternum 12.

Turning to FIG. 9, there is shown a second embodiment of an implantable elongate device 11, which is susceptible of being withdrawn (at the surgeon's option) prior to the surgeon's severing the patient's sternum during a re-do sternotomy. Simarlarly to the device 10', the device 11 may be of tapered configuration along the longitudinal dimension as shown in FIG. 9, in width and/or in depth. In an example of one such configuration, the width at one end 43 of the elongate member 11 may be within a range of approximately 2 and 5 centimeters, and a width of perhaps 0.5 centimeter at the other end 45 of the tapered elongate member 11. In such example, the depth of the elongate device 11 may be either uniform (perhaps 0.5 centimeter although the range described earlier with respect to the device 10' of FIG. 8 is also suitable) throughout its length or may progressively decrease along its length. In an example of decreasing depth, the depth at the one end 43 may be approximately 0.5 centimeter (although the range described earlier with respect to the device 10' of FIG. 8 is also suitable) and decreasing to approximately 0.25 centimeter at the other end 45. These dimensions, which may vary with an individual patient, are given as examples only and are not to be deemed exclusive of other dimensions or ranges thereof which would provide a suitable retrosternal tunnel. The elongate device 11 is made of an implantable material which is flexible and resilient, such as conventional medical grade silicone rubber, and does not include a hard elongate strip therein. The device 11 is implanted in the patient during wound closure, in the same manner as previously described with respect to the device 10' of FIG. 8.

Turning to FIG. 10 the fibrous tissue capsule 46, produced by the body about the device 11, is shown surrounding the device 11 and adhering to the posterior surface 32 of the sternum 12, the external wires not being shown for purposes of clarity. During a re-do sternotomy involving the patient in whom the device 11 had been implanted at the conclusion of a previous sternotomy, the surgeon exposes and identifies the end of the device 11 near the xiphoid process, opens the end of the fibrous tissue capsule 46 and longitudinally withdraws the device 11 from the capsule 46. Withdrawal is facilitated by the resistance of the fibrous tissue to form attachments to the device 11. Removal of the device 11 may occur either before or after the sternal wires are removed during the re-do sternotomy, although it is preferred that the wires be removed first (or at least cut and loosened) to preclude interference by the wires during withdrawal.

After removal of the elongate device 11 and the sternal wires, the surgeon proceeds to sever the sternum while utilizing the space created where the device 11 was disposed previously to its removal, providing a longitudinal pathway or retro-sternal tunnel 48 which may safely receive the sternal saw blade. As shown in FIG. 13, the foot 40 of the reciprocating type sternal saw blade 38 may be inserted in the space or retro-sternal tunnel 48 (at its exposed end) enveloped by the fibrous tissue layer 46, the tunnel 48 being used as a pathway for the foot 40 of the saw 38. Alternatively, an oscillating arcuate saw blade 36 of the type shown in FIG. 7 may be utilized, with the retro-sternal tunnel 48 of FIG. 13 providing a retro-sternal space for facilitating the re-do sternotomy.

FIG. 11 shows a second configuration of an elongate device 11' of the alternative embodiment of the device 11 shown in FIG. 9, which second configuration may be of circular or oval cross-section either uniform along its length or tapered. For example, the elongate member 11' may have an oval cross-section of approximately 1 centimeter major diameter and approximately 0.4 centimeter minor diameter, although other dimensions would be appropriate for providing a suitable retro-sternal tunnel, and the member 11' may be uniform along its length or tapered. FIG. 12 indicates the elongate device 11' of oval cross-section disposed within its fibrous tissue capsule 46 adherent to the posterior surface 32 of the sternum 12, the sternal wires not being shown for purposes of clarity. During a re-do sternotomy, the device 11' is longitudinally withdrawn from the fibrous capsule 46, producing a retro-sternal tunnel of oval cross-section but otherwise similar to the retro-sternal tunnel 48 shown in FIG. 13. During the re-do sternotomy, the surgeon proceeds to sever the sternum utilizing the oval retrosternal tunnel in the same manner as previously described with respect to utilization of the retro-sternal tunnel 48 shown in FIG. 13.

Alternatively the elongate device 11 or 11' need not be withdrawn prior to severing the sternum, as the device 11 or 11' may remain in place during the cutting of the sternum, particularly if an oscillating arcuate saw blade 36 were utilized.

Other embodiments of the present invention, and other configurations of the embodiments herein presented, may be developed without departing from the essential characteristics thereof. For example, the preferred embodiment of a resilient elongate envelope internally including a hard elongate member may have an outer configuration of circular or oval cross-section, either uniform or decreasing along its length. Further, configuration of elongate devices according to the present invention other than those described herein may be utilized. Accordingly, the invention should be limited only by the scope of the claims listed below.

We claim:

1. A method for producing an artificial retro-sternal space during closure of a longitudinally severed sternum, comprising the steps of:
   providing an implantable elongate member having a length approximately the length of the sternum,
   disposing said member longitudinally along the severed sternum and opposing the posterior surface thereof, and
   securing said disposed member to the sternum such that said member underlies the sternum when closed for assisting in guiding a sternum cutting device subsequently provided during a reserving of the sternum.

2. The method according to claim 1, above, wherein said disposed member is secured to the sternum while closing the sternum.

3. The method according to claim 1, above, wherein said disposed member is secured to the sternum such that said member underlies the sternum's severed edges when closed.

4. A method for producing a retro-sternal space in a patient, comprising the steps of:
   during closure of the patient's sternum during a sternotomy,
      providing an implantable elongate member,
      disposing said member longitudinally along and posteriad said sternum prior to closing said sternum, and
      securing said disposed member to said sternum while closing said sternum such that said member under lies said sternum when closed and is thereby implanted for assisting in guiding a sternum cutting device provided during a sternotomy of the sternum subsequent to the sternotomy during which said member was implanted.

5. The method according to claim 4, above, wherein said implantable elongate member provided during the providing step has a length approximately the length of said sternum.

6. The method according to claim 4, above, wherein said implantable elongate member provided during the providing step is flexible.

7. The method according to claim 4, above, wherein said member underlies the severed edges of said sternum when closed and said member is implanted.

8. The method according to claim 4 above, wherein:
   during the providing step a plaint implantable elongate member including a surface is provided, and
   during the securing step said pliant member surface contacts and conforms to the posterior surface of said sternum.

9. A method for producing and utilizing a retro-sternal space in a patient, comprising the steps of:
   during closure of the patient's sternum during a sternotomy,
      providing an implantable elongate member,
      disposing said member longitudinally along and posteriad said sternum prior to closing said sternum, and
      securing said disposed member to said sternum while closing said sternum such that said member underlies said sternum when closed and is thereby implanted; and during a sternotomy of said sternum subsequent to the sternotomy during which said member was implanted, locating an end of said implanted member, lengthwise withdrawing said member to provide a retro-sternal tunnel in the space formerly occupied by said member, positioning a sternum cutting device at an end of said retro-sternal tunnel, and longitudinally severing said sternum with said cutting device passing along said retro-sternal tunnel.

10. A method for producing and utilizing a retro-sternal spaced in a patient, comprising the steps of:

during closure of the patient's sternum during a sternotomy, providing an implantable elongate member, disposing said member longitudinally along and posteriad said sternum prior to closing said sternum, and securing said disposed member to said sternum while closing said sternum such that said member underlies said sternum when closed and is thereby implanted; and during a sternotomy of said sternum subsequent to the sternotomy during which said elongate member was implanted, locating an end of said elongate member, positioning a sternum cutting device at said located end, and longitudinally severing said sternum using said cutting device with said implanted member shielding the patient's heart from said cutting device.

11. A method for producing and utilizing a retrosternal space in a patient, comprising the steps of:

during closure of the patient's sternum during a sternotomy, providing an implantable elongate member, disposing said member longitudinally along and posteriad said sternum prior to closing said sternum, and securing said disposed member to said sternum while closing said sternum such that said member underlies said sternum when closed and is thereby implanted; and during a sternotomy of said sternum subsequent to the sternotomy during which said elongate member was implanted, positioning a sternum cutting device at an end of said sternum overlying said implanted member, and longitudinally severing said sternum using said cutting device with said implanted member shielding the patient's heart from said cutting device.

12. A method for producing a retro-sternal space in a patient, comprising the steps of:

during closure of the patient's sternum during a sternotomy, providing an implantable elongate member including a chamber therein extending substantially along the length of said implantable member, said chamber containing a hard elongate member enclosed therein, disposing said implantable member longitudinally along and posteriad said sternum prior to closing said sternum, and securing said disposed implantable member to said sternum while closing said sternum such that said implantable member and said hard member underlie said sternum when closed and said implantable member is implanted.

13. The method according to claim 12, above, further including the steps of:

during a sternotomy of said sternum subsequent to the sternotomy during which said implantable elongate member was implanted, positioning a sternum cutting device at an end of said sternum overlying said implanted member, and longitudinally severing said sternum using said cutting device with said enclosed hard elongate member shielding the patient's heart from said cutting device.

14. The method according to claim 12, above, wherein said implantable elongate member provided during the providing step is pliant.

15. The method according to claim 13, above, wherein:

during the providing step a pliant implantable elongate member including a surface is provided; and during the securing step said pliant member surface contacts and conforms to the posterior surface of said sternum.

* * * * *